United States Patent
Chun et al.

(10) Patent No.: US 9,764,052 B2
(45) Date of Patent: Sep. 19, 2017

(54) VACUUM ASSISTED DEHYDRATION SYSTEM

(71) Applicant: Hankookin, Inc., Raleigh, NC (US)

(72) Inventors: James Jiwen Chun, Raleigh, NC (US); Andrew Youngho Chun, Raleigh, NC (US); Angela Soyoung Chun, Raleigh, NC (US); Jennifer Miseong Chun, Raleigh, NC (US)

(73) Assignee: HANKOOKIN, INC., Raleigh, NC (US)

( * ) Notice: Subject to any disclaimer, the term of this patent is extended or adjusted under 35 U.S.C. 154(b) by 478 days.

(21) Appl. No.: 14/217,370

(22) Filed: Mar. 17, 2014

(65) Prior Publication Data

US 2014/0283408 A1    Sep. 25, 2014

Related U.S. Application Data

(60) Provisional application No. 61/803,196, filed on Mar. 19, 2013.

(51) Int. Cl.
*A61L 9/00* (2006.01)
*A61L 2/00* (2006.01)

(52) U.S. Cl.
CPC .. *A61L 9/00* (2013.01); *A61L 2/00* (2013.01)

(58) Field of Classification Search
CPC ..................................... A61L 2/00; A61L 9/00
USPC .................................................... 34/408, 312
See application file for complete search history.

(56) References Cited

U.S. PATENT DOCUMENTS

| | | | | |
|---|---|---|---|---|
| 58,425 | A * | 10/1866 | Jenks ........................ | F26B 5/04 34/408 |
| 90,545 | A * | 5/1869 | Hughes ..................... | F26B 5/04 34/387 |
| 1,415,623 | A * | 5/1922 | Atkinson .................. | F26B 5/04 34/408 |
| 1,421,685 | A * | 7/1922 | Glessner ................... | F26B 5/04 34/92 |

(Continued)

FOREIGN PATENT DOCUMENTS

| | | | | |
|---|---|---|---|---|
| AT | WO 2004011863 | A1 * | 2/2004 | ................. F26B 5/04 |
| DE | 2404068 | A1 * | 8/1975 | ............ F17C 13/002 |

*Primary Examiner* — Kenneth Rinehart
*Assistant Examiner* — Logan Jones
(74) *Attorney, Agent, or Firm* — Ash Tankha; Lipton, Weinberger & Husick

(57) ABSTRACT

A vacuum assisted dehydration system including a vacuum chamber, a gas compressor, a heating coil, and a vacuum pump is provided. A sealing member removably attached to an opening of the vacuum chamber is opened to introduce one or more instruments into the vacuum chamber. The gas compressor, in fluid communication with the vacuum chamber, recirculates a pressurized gas into the vacuum chamber. The heating coil within the vacuum chamber heats the recirculating gas, which contacts the instruments positioned therein and transfers heat energy into interstitial cavities and to surfaces of the instruments or onto other moist components, for example, hands to vaporize moisture present therein. The vacuum pump, in fluid communication with the vacuum chamber, creates a negative gas pressure in the vacuum chamber to exhaust the vaporized moisture entrained in the heated recirculating gas from the vacuum chamber to dehydrate the instruments or the moist components.

10 Claims, 13 Drawing Sheets

FIG. 9B

(56) References Cited

U.S. PATENT DOCUMENTS

| | | | | | |
|---|---|---|---|---|---|
| 1,799,248 | A | * | 4/1931 | Reinhardt | H01M 4/23 34/213 |
| 2,127,638 | A | * | 8/1938 | Brandwood | D06C 7/00 28/167 |
| 2,296,546 | A | * | 9/1942 | Toney | B27K 1/00 34/411 |
| 2,799,947 | A | * | 7/1957 | Elwess | F26B 9/085 34/102 |
| 3,010,216 | A | * | 11/1961 | Ravet | F26B 5/04 34/403 |
| 3,605,278 | A | * | 9/1971 | Ramsay | F26B 5/04 34/92 |
| 4,876,802 | A | * | 10/1989 | Gergely | A61K 9/0007 34/408 |
| 5,433,020 | A | * | 7/1995 | Leech, Jr. | F26B 11/049 34/403 |
| 5,806,204 | A | * | 9/1998 | Hoffman | D06F 58/12 34/605 |
| 6,367,311 | B1 | * | 4/2002 | Garg | F26B 5/04 73/40 |
| 6,511,550 | B1 | * | 1/2003 | Noestheden | B08B 3/00 134/21 |
| 6,524,539 | B1 | * | 2/2003 | Katschnig | A61L 2/12 422/186.07 |
| 8,458,922 | B2 | * | 6/2013 | Parisi | A45D 27/48 108/115 |
| 2008/0115382 | A1 | * | 5/2008 | Ramhold | B01D 1/0082 34/406 |
| 2008/0273941 | A1 | * | 11/2008 | Van Cor | F16B 33/02 411/426 |
| 2009/0158614 | A1 | * | 6/2009 | Singh | F26B 5/04 34/474 |
| 2012/0304484 | A1 | * | 12/2012 | Ramhold | B01D 1/0082 34/312 |

\* cited by examiner

VACUUM ASSISTED DEHYDRATION SYSTEM

CROSS REFERENCE TO RELATED APPLICATIONS

This application claims priority to and the benefit of provisional patent application No. 61/803,196 titled "Vacuum Assisted Dehydration System", filed in the United States Patent and Trademark Office on Mar. 19, 2013. The specification of the above referenced patent application is incorporated herein by reference in its entirety.

BACKGROUND

Maintenance of dental instruments, for example, dental turbines and dental handpieces, is a difficult task. Rotating components incorporated in dental instruments are delicate and complex devices. In a clinical assessment, cleaning and lubrication of high speed handpieces have been found to be critical in determining their performance and durability. A manufacturer's instructions for cleaning, lubrication, and sterilization should be followed correctly to ensure the efficiency of the process and the longevity of the handpieces.

Sterilization of medical and dental instruments is required in medical offices and dental offices. Moist heat sterilization under high pressure and a high temperature, which are well known in the art, are used for sterilizing medical and dental instruments. However, moist heat sterilization at high pressure and high temperature can cause permanent damage to medical and dental instruments, for example, high speed handpieces. Dental high speed handpieces are known to be very difficult and costly to moist heat sterilize and maintain. One possible cause of damage to a high speed handpiece is chemical corrosion of a metal component therewithin due to the presence of water or moisture on the surfaces or interstitial cavities of the high speed handpiece. Moisture that resides in interstitial cavities of high speed handpieces is generally not removed by conventional pre-sterilization cleaning methods such as manual scrubbing, air driven oiling using specialized appliances, for example, Assistina™ of the W & H Group, Austria, etc. Moisture tends to condense within the interstitial cavities even after substantial pre-sterilization cleaning due to the complex geometries and interstitial cavities in the high speed handpieces. This moisture may mix with lubrication oil that may be present in the high speed handpiece and cause damage to the high speed handpiece during sterilization at elevated temperatures and during normal usage of the high speed handpiece. If water and moisture can be completely removed during the pre-sterilization cleaning process, damage to the high speed handpiece during sterilization and normal usage can be substantially reduced.

Hence, there is a long felt but unresolved need for a vacuum assisted dehydration system that dehydrates one or more instruments, for example, medical instruments, dental instruments, etc., using a negative gas pressure to remove moisture from the instruments, for example, before a lubrication process to maximize lubrication of instrument turbines to extend the useful life of the instruments.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The vacuum assisted dehydration system disclosed herein addresses the above mentioned need for dehydrating one or more instruments using a negative gas pressure. As used herein, the term "dehydration" refers to a process of removing moisture from an interstitial cavity or a surface of an object such as a dental instrument. Also, as used herein, the term "instruments" refers, for example, to components, devices, tools, appliances, apparatuses, equipment, etc., used in fields such as medicine, dentistry, etc. The instruments comprise, for example, dental instruments such as a high speed handpiece, a slow speed motor attachment, a cheek retractor, a tongue retractor, etc., medical instruments such as needles, scalpel blades, etc. Also, as used herein, "negative gas pressure" refers to a state of vacuum created in an inner enclosed space within a closed chamber. The vacuum assisted dehydration system disclosed herein can be used to remove moisture from the instruments, for example, before a lubrication process to maximize lubrication of instrument turbines to extend the useful life of the instruments.

The vacuum assisted dehydration system disclosed herein comprises a generally cylindrical vacuum chamber, a sealing member, and a vacuum pump. The vacuum chamber defines an inner enclosed space for accommodating one or more instruments, for example, dental instruments. The sealing member is removably attached to a first opening defined at a first opposing end of the vacuum chamber. The sealing member is opened to allow one or more instruments to be introduced into the inner enclosed space of the vacuum chamber. In an embodiment, the sealing member is a metallic cap concentrically aligned with a washer. The metallic cap is fastened through threads configured at the first opening defined at the first opposing end of the vacuum chamber. In another embodiment, the sealing member is a push fit seal comprising a metallic cap and a washer. The sealing member push fits to the first opening defined at the first opposing end of the vacuum chamber to facilitate an air tight seal of the vacuum chamber. In an embodiment, the sealing member is made of a metallic material having a low coefficient of thermal expansion to avoid expansion of the sealing member due to heat produced by the heating coil.

The vacuum pump is operably connected to a second opening defined at a second opposing end of the vacuum chamber. The vacuum pump is in fluid communication with the vacuum chamber via the second opening. The vacuum pump is, for example, a multistage centrifugal vacuum pump or a multistage reciprocating vacuum pump. In an embodiment, the vacuum pump is operably connected to the second opening of the vacuum chamber through a flexible tube, for example, a hose, a pipe, etc. The vacuum pump creates a negative gas pressure in the inner enclosed space of the vacuum chamber to dehydrate the accommodated instruments after the vacuum chamber is closed by the sealing member. In an embodiment, the vacuum assisted dehydration system disclosed herein further comprises a heating coil positioned on an inner surface wall of the vacuum chamber. The heating coil heats a recirculating gas in the inner enclosed space of the vacuum chamber, which facilitates the removal of moisture from the instruments placed in the vacuum chamber and accelerates the dehydration of the instruments.

In an embodiment, the vacuum assisted dehydration system disclosed herein further comprises a gas compressor and a gas inlet port, in addition to the generally cylindrical vacuum chamber, the sealing member, the heating coil, and the vacuum pump disclosed above. The vacuum chamber comprises a surface wall defining an inner enclosed space for accommodating one or more instruments. The surface wall of the vacuum chamber is made of, for example, aluminum, stainless steel, etc. The surface wall of the vacuum chamber reflects heat. In an embodiment, the vacuum assisted dehydration system disclosed herein further comprises a condenser in upstream communication with the vacuum pump via a vacuum pump outlet pipe, and in downstream communication with the gas compressor via a condenser outlet pipe. The gas compressor is positioned proximal to and in fluid communication with the vacuum chamber via an inlet tube. The gas compressor recirculates a gas pressurized to a preset pressure into the inner enclosed space of the vacuum chamber via the inlet tube. In an embodiment, the gas is an inert gas, for example, argon. The gas compressor pressurizes the inert gas to a preset pressure in a range of between about 15 psig to about 40 psig. For example, the gas pressure is preset at a pressure of about 16 psig. The gas compressor pumps the recirculating gas via the inlet tube to the inner enclosed space within the vacuum chamber.

The gas inlet port is defined on the surface wall of the vacuum chamber. The gas inlet port is in fluid communication with the gas compressor via the inlet tube. The recirculating gas from the gas compressor is fed into the inner enclosed space of the vacuum chamber through the gas inlet port via the inlet tube. The heating coil is operably positioned on the inner surface wall of the vacuum chamber. The heating coil is, for example, an electric heating coil. The heating coil heats the recirculating gas in the inner enclosed space of the vacuum chamber to a preset temperature of, for example, between about 30° Celsius (C) to about 75° C. The heated recirculating gas contacts the instruments positioned in the inner enclosed space of the vacuum chamber and transfers heat energy into interstitial cavities and to the surfaces of the instruments to vaporize moisture present in the interstitial cavities and on the surfaces of the instruments. The interstitial cavities comprise, for example, needle grooves, narrow and deep fluid transfer lines, etc., in the instruments. The surfaces of the instruments, for example, cover a total surface area of the instruments including surfaces defined by the interstitial cavities. In an embodiment, the vacuum assisted dehydration system further comprises safety switches operably connected to the heating coil to regulate the temperature to a predetermined level in the inner enclosed space of the vacuum chamber.

The vacuum pump creates a negative gas pressure in the inner enclosed space of the vacuum chamber to dehydrate the accommodated instruments after the vacuum chamber is closed by the sealing member, and exhausts the vaporized moisture entrained in the heated recirculating gas from the inner enclosed space of the vacuum chamber to the condenser. In an embodiment, the vacuum assisted dehydration system further comprises one or more pressure control valves operably connected to the vacuum pump for controlling an amount of the negative gas pressure created within the inner enclosed space of the vacuum chamber to protect the accommodated instruments within the vacuum chamber.

The condenser, operably connected to and in fluid communication with the vacuum pump of the vacuum assisted dehydration system, receives the vaporized moisture entrained in the heated recirculating gas from the vacuum pump. The vaporized moisture entrained in the recirculating gas is exhausted from the vacuum chamber by the vacuum pump to the condenser. The condenser condenses and reduces moisture from the vaporized moisture entrained in the heated recirculating gas, for example, by contacting the vaporized moisture entrained in the heated recirculating gas with a heat exchange surface such as a coil through which a refrigerant is recirculating at a temperature of, for example, about 10° C. to about −2° C. When the vaporized moisture entrained in the heated recirculating gas contacts the refrigerant coil, the moisture condenses out and is drained out from the condenser. The moisture reduced, low humidity recirculating gas is exhausted from the condenser to the gas compressor.

In an embodiment, instead of the vacuum pump, the vacuum assisted dehydration system disclosed herein further comprises a suction line, for example, a medical suction line or a dental suction line, operably connected to the second opening of the vacuum chamber. The suction line produces a vacuum having a vacuum pressure of, for example, about 29 inches of mercury within the inner enclosed space of the vacuum chamber.

In an embodiment, a vacuum assisted dehydration system for dehydrating one or more components containing moisture on the surface of the components, herein referred to as "moist components", for example, a user's moist hands, moist gloves, etc., in a dental or a medical environment is provided. In this embodiment, the vacuum assisted dehydration system disclosed herein comprises the generally cylindrical vacuum chamber, the condenser, the gas compressor, the gas inlet port, the heating coil, and the vacuum pump, without the sealing member. In this embodiment, the first opening defined at the first opposing end of the vacuum chamber is configured to receive the moist components into the inner enclosed space of the vacuum chamber. The recirculating gas received from the gas compressor is heated by the heating coil and the heated recirculating gas contacts the moist components positioned in the inner enclosed space of the vacuum chamber and transfers heat energy to the moist components to vaporize moisture off the moist components. The vacuum pump creates a negative gas pressure in the inner enclosed space of the vacuum chamber to dehydrate the moist components and exhausts the vaporized moisture entrained in the heated recirculating gas from the inner enclosed space of the vacuum chamber to the condenser. The vacuum assisted dehydration system disclosed herein provides a transient dehydration region in the inner enclosed space of the vacuum chamber for dehydrating the moist components by recirculating the gas from the gas compressor into the inner enclosed space of the vacuum chamber, heating the recirculating gas using the heating coil, allowing the heated recirculating gas to contact the moist components, and exhausting the vaporized moisture entrained in the heated recirculating gas from the moist components via the vacuum pump.

In an embodiment, the vacuum assisted dehydration system disclosed herein further comprises a rotary disk assembly positioned on an inner surface wall of the vacuum chamber. The rotary disk assembly comprises a disk member and an electric motor. The disk member is axially aligned and fixedly connected to the electric motor. The disk member fixedly accommodates one or more instruments. The electric motor rotates the disk member at a sufficient speed to generate a centrifugal force sufficient to force the moisture present in the interstitial cavities and on the surfaces of the accommodated instruments to open ends or open surfaces of the accommodated instruments for removal by the recirculating gas fed by the gas compressor into the inner enclosed space of the vacuum chamber, by the recirculating gas heated by the heating coil, and by the negative gas pressure created in the vacuum chamber by the vacuum pump.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a structure or a method step referenced by a numeral in a drawing carries over to the description of that structure or method step shown by that same numeral in any subsequent drawing herein.

DETAILED DESCRIPTION OF THE INVENTION

Figure 1:
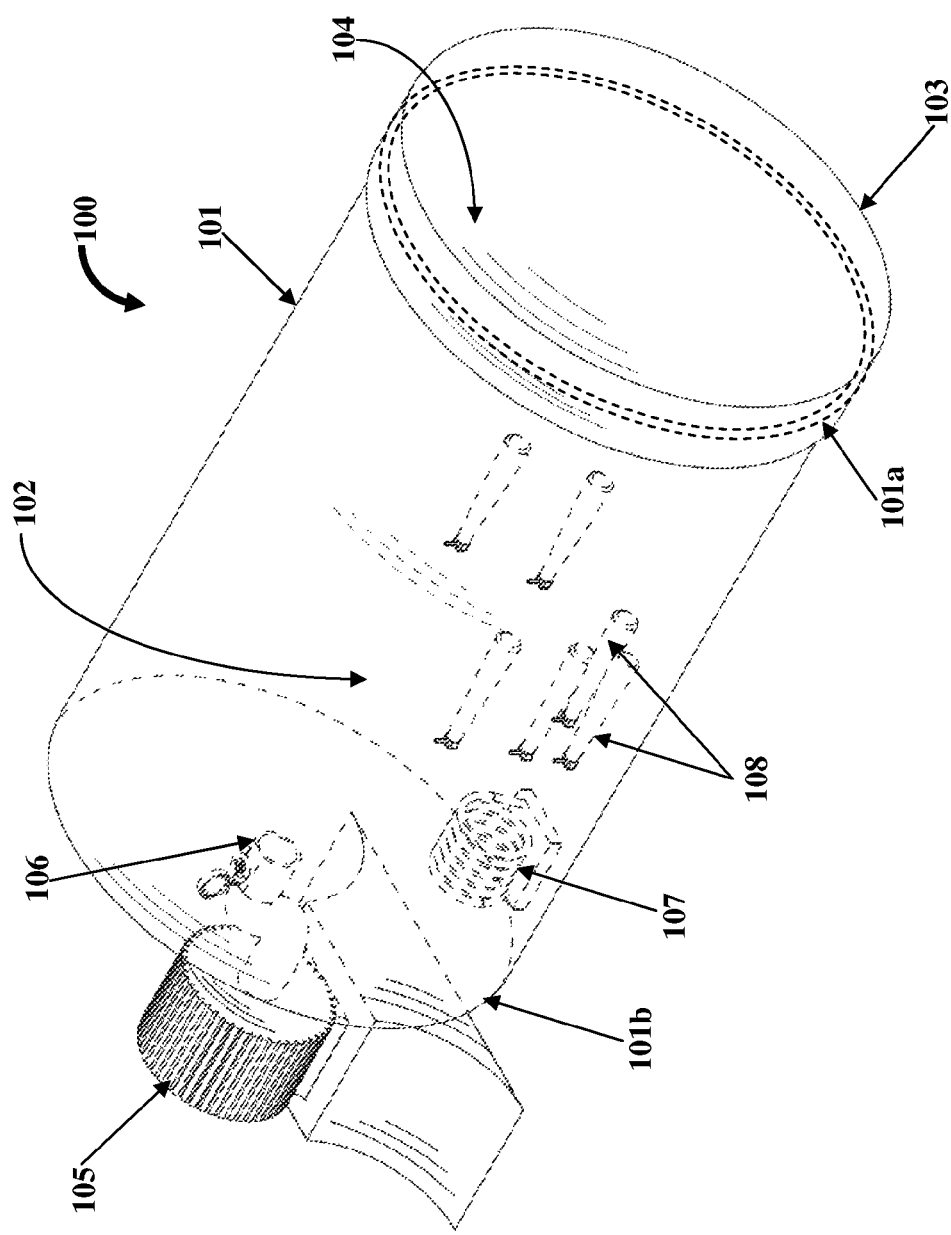
FIG. 1 exemplarily illustrates a top perspective view of a vacuum assisted dehydration system comprising a generally cylindrical vacuum chamber, a sealing member, and a vacuum pump.

FIG. 1 exemplarily illustrates a top perspective view of a vacuum assisted dehydration system 100 comprising a generally cylindrical vacuum chamber 101, a sealing member 103, and a vacuum pump 105. The vacuum assisted dehydration system 100 dehydrates one or more instruments 108 by creating a negative gas pressure within the vacuum chamber 101. As used herein, the term "dehydration" refers to a process of removing moisture or water, herein "moisture", from an interstitial cavity or a surface of an object such as a dental instrument. Also, as used herein, the term "instruments" refers, for example, to components, devices, tools, appliances, apparatuses, equipment, etc., used in fields such as medicine, dentistry, etc. The instruments 108 comprise, for example, dental instruments such as a high speed hand piece, a slow speed motor attachment, a cheek retractor, a tongue retractor, etc., medical instruments such as needles, scalpel blades, etc. Also, as used herein, "negative gas pressure" refers to a state of vacuum created in an inner enclosed space 102 within the vacuum chamber 101. The vacuum chamber 101 defines an inner enclosed space 102 therewithin for accommodating one or more instruments 108. The vacuum chamber 101 is configured, for example, as an air tight metal cylinder. The vacuum chamber 101 is manufactured in predetermined sizes depending on the sizes of the instruments 108 to be accommodated therewithin. The vacuum chamber 101 is made of metallic materials, for example, aluminum, stainless steel, etc. The sealing member 103 is removably attached to a first opening 104 defined at a first opposing end 101a of the vacuum chamber 101. The sealing member 103 is configured to be positioned over the first opening 104 to open and close the vacuum chamber 101 to allow instruments 108 to be introduced into and removed out of the inner enclosed space 102 of the vacuum chamber 101.

The vacuum pump 105 is operably connected to a second opening 106 defined at a second opposing end 101b of the vacuum chamber 101. The vacuum pump 105 is in fluid communication with the vacuum chamber 101 via the second opening 106. The vacuum chamber 101 extends along a horizontal direction from the first opposing end 101a to the second opposing end 101b. The vacuum pump 105 creates a preset negative gas pressure, for example, a negative pressure of between about 2 inches of mercury to about 29 inches of mercury in the inner enclosed space 102 of the vacuum chamber 101 to dehydrate the accommodated instruments 108 after the vacuum chamber 101 is closed by the sealing member 103 and the vacuum pump 105 is turned on.

In an embodiment, the vacuum assisted dehydration system 100 disclosed herein further comprises a heating coil 107 for heating a recirculating gas in the inner enclosed space 102 of the vacuum chamber 101, which facilitates removal of moisture from the instruments 108 placed in the vacuum chamber 101 and accelerates the dehydration of the accommodated instruments 108.

Figure 2:
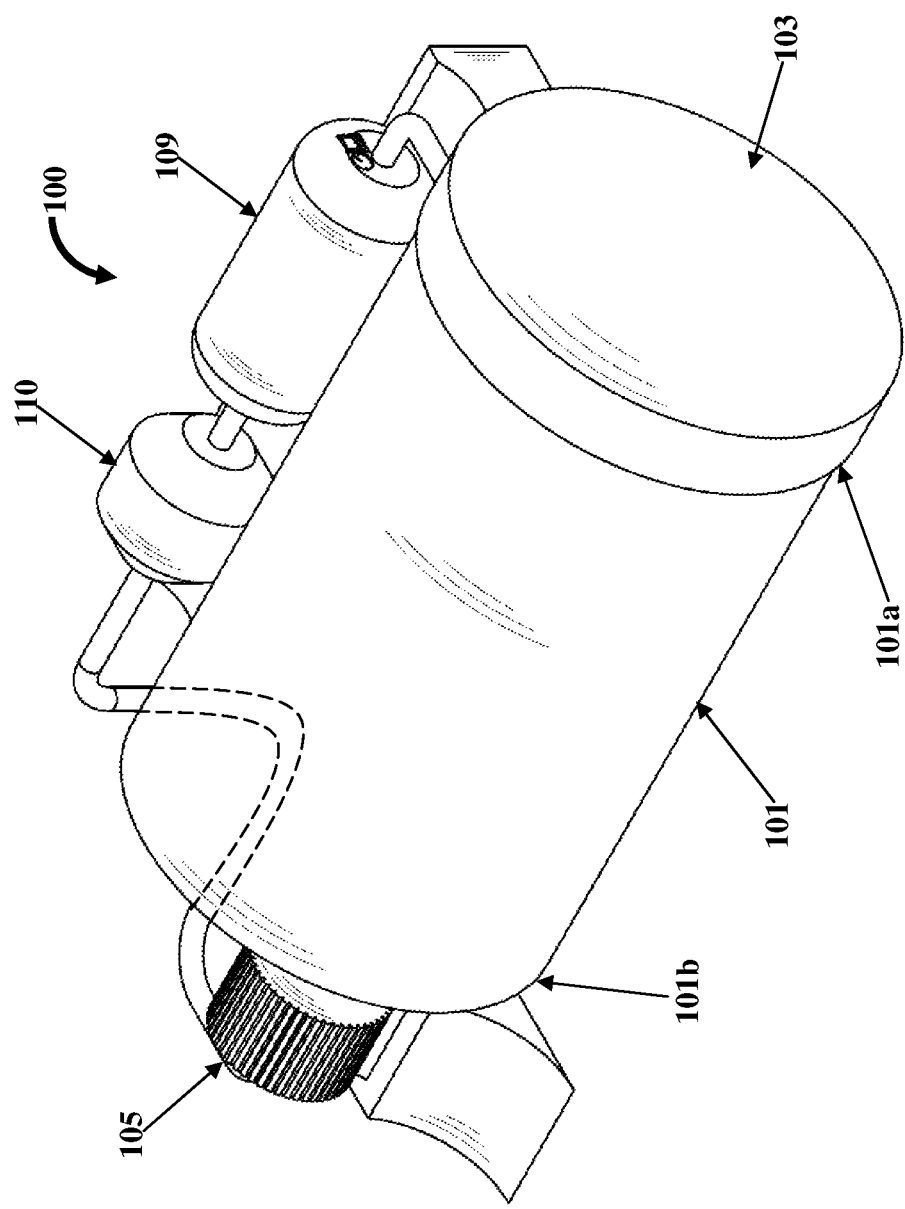
FIG. 2 exemplarily illustrates a top perspective view of an embodiment of the vacuum assisted dehydration system comprising the generally cylindrical vacuum chamber, the sealing member, the vacuum pump, a condenser, and a gas compressor.

FIG. 2 exemplarily illustrates a top perspective view of an embodiment of the vacuum assisted dehydration system 100. In this embodiment, in addition to the generally cylindrical vacuum chamber 101, the sealing member 103, and the vacuum pump 105 disclosed in the detailed description of FIG. 1, the vacuum assisted dehydration system 100 further comprises a gas compressor 109 and a condenser 110. The gas compressor 109 is, for example, a small sized hermetically sealed gas compressor, used to recirculate gas pressurized to a preset pressure between about 16 psig to about 20 psig into the vacuum chamber 101. As an example, in many dental offices, the pressurized gas or compressed air is also available from dental compressors that produce air pressure up to, for example, about 29 inches of mercury. In another example, the pressurized gas is also available from dental compressors that produce pressurized gas, for example, at about 15 psig to about 40 psig.

Figures 3A, 3B:
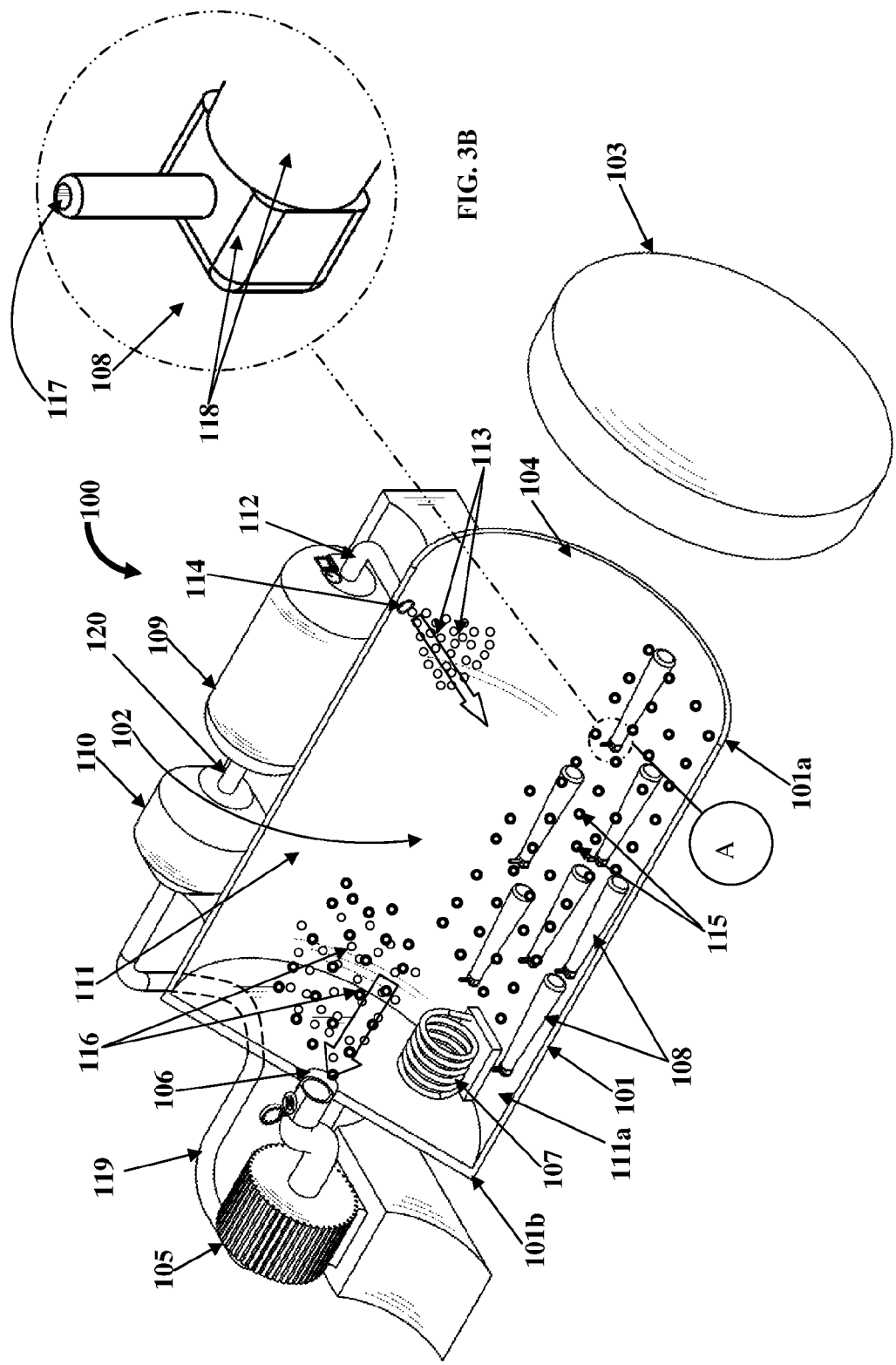
FIG. 3A exemplarily illustrates a cutaway view of the embodiment of the vacuum assisted dehydration system shown in FIG. 2, showing one or more instruments accommodated in an inner enclosed space of the vacuum chamber.
FIG. 3B exemplarily illustrates an enlarged view of a portion marked A in FIG. 3A of the embodiment of the vacuum assisted dehydration system, showing interstitial cavities and surfaces of an instrument.

The vacuum pump 105, operably connected at the second opposing end 101b of the vacuum chamber 101 and in fluid communication with the vacuum chamber 101, creates a preset negative gas pressure, for example, a negative pressure of between about 2 inches of mercury to about 29 inches of mercury in the vacuum chamber 101 to dehydrate the instruments 108 accommodated in the vacuum chamber 101 as exemplarily illustrated in FIG. 3A. The condenser 110 is operably connected to and in fluid communication with the vacuum pump 105 to receive vaporized moisture entrained in the recirculating gas from the vacuum pump 105. The condenser 110 condenses out and reduces moisture from the vaporized moisture entrained in the recirculating gas as disclosed in the detailed description of FIGS. 3A-3B.

As used herein, "gas" refers to air or an inert gas that is recirculated in the loop comprising the vacuum chamber 101, the vacuum pump 105, the condenser 110, and the gas compressor 109. The recirculating gas is supplied at a low to moderate pressure, preset at a pressure of between about 15 psig to about 40 psig from the gas compressor 109 to the inner enclosed space 102 within the vacuum chamber 101 exemplarily illustrated in FIG. 3A. The inner enclosed space 102 within the vacuum chamber 101 is maintained at a negative pressure, for example, preset at a negative pressure of between about 2 inches of mercury and about 29 inches of mercury to allow the moisture in the interstitial cavities 117 and on surfaces 118 of the instruments 108 exemplarily illustrated in FIG. 3B, to volatize off the instruments 108 and be entrained in the recirculating gas circulating in the loop. In an embodiment, the recirculating gas in the inner enclosed space 102 within the vacuum chamber 101 is heated by a heating coil 107 positioned in the inner enclosed space 102 as exemplarily illustrated in FIG. 3A, to a preset temperature of, for example, between about 30° Celsius (C.) to about 75° C. to facilitate the removal of the moisture from the instruments 108 by increasing the temperature of the instruments 108 and the moisture contained in the interstitial cavities 117 or surfaces 118 of the instruments 108. The vaporized moisture entrained in the recirculating gas from the vacuum chamber 101 is exhausted by the vacuum pump 105 to the condenser 110, where the moisture in the recirculating gas is condensed out by dropping the temperature of the vaporized moisture entrained in the recirculating gas to a preset temperature, for example, between about −2° C. and about 10° C. in the condenser 110.

FIG. 3A exemplarily illustrates a cutaway view of the embodiment of the vacuum assisted dehydration system 100 shown in FIG. 2, showing one or more instruments 108 accommodated in the inner enclosed space 102 of the vacuum chamber 101. As exemplarily illustrated in FIG. 3A, the vacuum assisted dehydration system 100 disclosed herein comprises the vacuum pump 105, the condenser 110, the gas compressor 109, the generally cylindrical vacuum chamber 101, the heating coil 107, and the sealing member 103. The vacuum chamber 101 comprises a surface wall 111 defining the inner enclosed space 102. The surface wall 111 of the vacuum chamber 101 is, for example, made of aluminum. The inner enclosed space 102 accommodates one or more instruments 108. The surface wall 111 of the vacuum chamber 101 reflects heat. The sealing member 103 is removably attached to a first opening 104 defined at a first opposing end 101a of the vacuum chamber 101. The sealing member 103 is used to open the vacuum chamber 101 to allow instruments 108 to be introduced into the inner enclosed space 102 of the vacuum chamber 101 and is thereafter closed prior to the vacuum pump 105 being turned on.

In this embodiment, the condenser 110 is in upstream communication with the vacuum pump 105 via a vacuum pump outlet pipe 119, and in downstream communication with the gas compressor 109 via a condenser outlet pipe 120. The condenser 110 condenses and reduces the moisture in a recirculating gas, for example, by lowering the temperature of the recirculating gas by contacting the recirculating gas with a heat exchange surface such as a coil 110a through which a refrigerant is circulating at a temperature preset, for example, at a temperature between about 10° C. to about −2° C. as exemplarily illustrated in FIG. 10. When the recirculating gas with the entrained moisture 116 contacts the refrigerant coil 110a, the moisture condenses out and is drained from the condenser 110.

The recirculating gas with the low humidity, reduced moisture content from the condenser 110 is fed to the gas compressor 109. The gas compressor 109 is positioned proximal to and in fluid communication with the vacuum chamber 101 via an inlet tube 112. The gas compressor 109 feeds the recirculating gas 113 into the inner enclosed space 102 of the vacuum chamber 101 via the inlet tube 112. In an embodiment, the recirculating gas 113 is an inert gas, for example, argon. A gas inlet port 114 is defined on the surface wall 111 of the vacuum chamber 101. The gas inlet port 114 is in fluid communication with the gas compressor 109 via the inlet tube 112. The heating coil 107 is operably positioned proximal to the second opening 106 on an inner surface wall 111a of the vacuum chamber 101. The heating coil 107 placed proximal to the one or more instruments 108 heats the recirculating gas 113 in the inner enclosed space 102 of the vacuum chamber 101 to a preset temperature, for example, a temperature preset between about 30° C. and about 75° C. The recirculating gas 113 heated by the heating coil 107, contacts the instruments 108 positioned in the inner enclosed space 102 of the vacuum chamber 101 and transfers heat energy into the interstitial cavities 117 and to the surfaces 118 of the accommodated instruments 108 to vaporize moisture 115 present in the interstitial cavities 117 and on the surfaces 118 of the accommodated instruments 108 as exemplarily illustrated in FIG. 3B, which shows an enlarged view of a portion marked A in FIG. 3A. As exemplarily illustrated in FIG. 3B, the interstitial cavities 117 comprise, for example, needle grooves, narrow and deep fluid transfer lines, etc., in the instruments 108. The surfaces 118 of the instruments 108, for example, cover the total surface area of the instruments 108 including surfaces defined by the interstitial cavities 117.

As exemplarily illustrated in FIG. 3A, the vacuum pump 105 is operably connected to a second opening 106 defined at the second opposing end 101b of the vacuum chamber 101. The vacuum pump 105 is in fluid communication with the vacuum chamber 101 via the second opening 106. The vacuum pump 105 creates a negative gas pressure, for example, a negative pressure preset to between about 2 inches of mercury and about 29 of inches mercury, in the inner enclosed space 102 of the vacuum chamber 101 to vaporize the moisture 115 off the accommodated instruments 108 and exhausts the vaporized moisture entrained in the recirculating gas 116, which may optionally be heated by the heating coil 107 positioned in the inner enclosed space 102 of the vacuum chamber 101. The vacuum pump 105 is in fluid communication with the condenser 110 via the vacuum pump outlet pipe 119. In an embodiment, the condenser 110, operably connected to and in fluid communication with the vacuum pump 105, receives the vaporized moisture entrained in the heated recirculating gas 116 from the vacuum pump 105 via the vacuum pump outlet pipe 119. The condenser 110 condenses and reduces moisture from the vaporized moisture entrained in the heated recirculating gas 116 exhausted from the vacuum chamber 101 by the vacuum pump 105, and feeds a moisture reduced, low humidity recirculating gas into the gas compressor 109 via the condenser outlet pipe 120.

The moisture reduced, low humidity recirculating gas from the condenser 110 is fed to the gas compressor 109 and compressed to a preset pressure, for example, a pressure preset to between about 16 psig and 25 psig by the gas compressor 109 and is recirculated back to the vacuum chamber 101. In an embodiment, the recirculated gas 113 fed to the vacuum chamber 101 is heated by the heating coil 107 to a preset temperature, for example, a temperature of between about 30° C. to about 75° C. in the vacuum chamber 101.

Figure 4A:
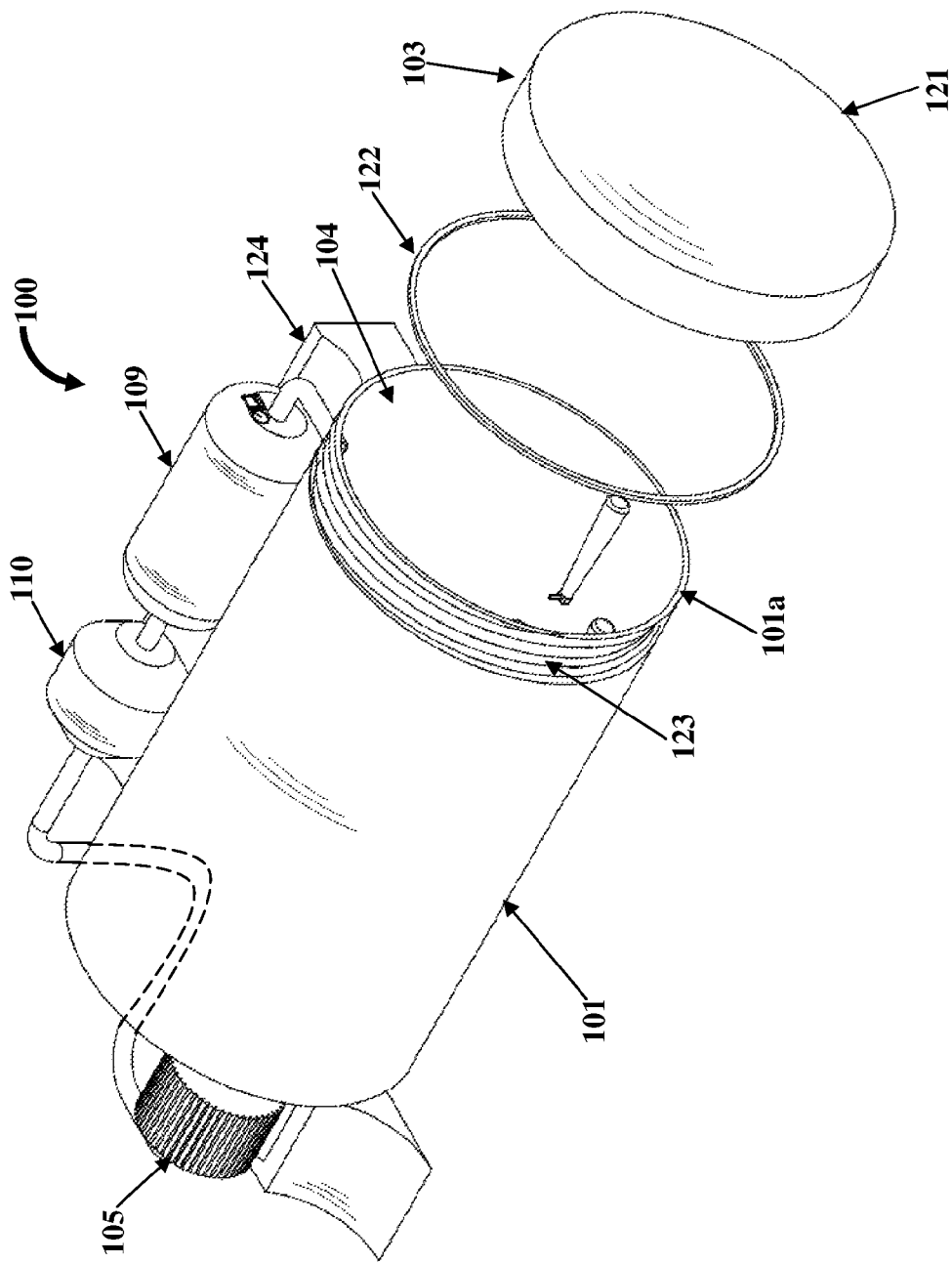
FIG. 4A exemplarily illustrates a top perspective view of an embodiment of the vacuum assisted dehydration system, showing a threadable connection of the sealing member to an opening of the vacuum chamber.
Figure 4B:
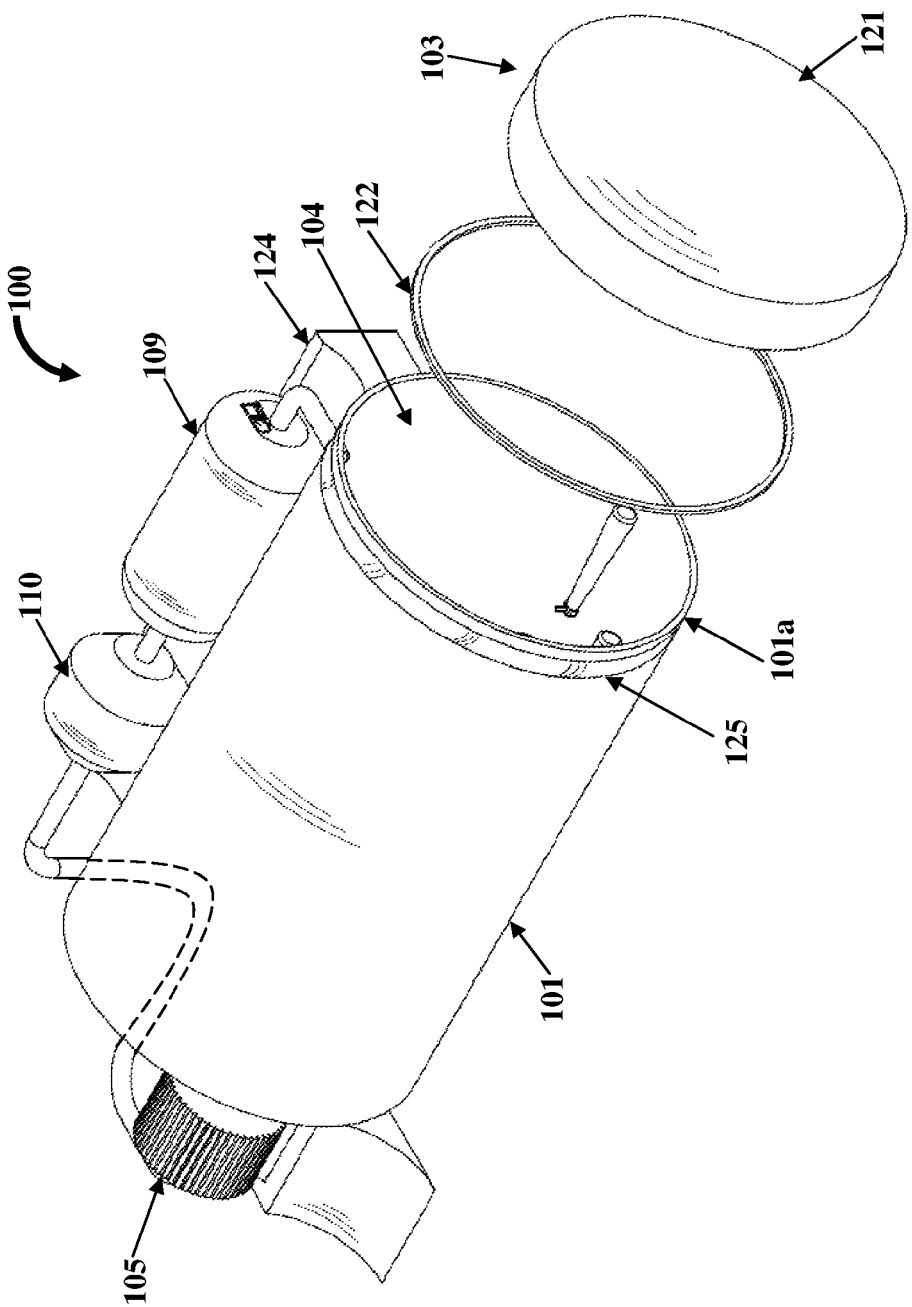
FIG. 4B exemplarily illustrates a top perspective view of another embodiment of the vacuum assisted dehydration system, showing a push fit connection of the sealing member to an opening of the vacuum chamber.

FIGS. 4A-4B exemplarily illustrate top perspective views of embodiments of the vacuum assisted dehydration system 100, showing embodiments of the sealing member 103. FIG. 4A shows a threadable connection of the sealing member 103 to an opening 104 of the vacuum chamber 101. The sealing member 103 is configured, for example, as an air tight cap. In an embodiment, the sealing member 103 is a metallic cap 121 concentrically aligned with a rubber washer 122. The metallic cap 121 is fastened through threads 123 configured at the first opening 104 defined at the first opposing end 101a of the vacuum chamber 101 as exemplarily illustrated in FIG. 4A. In FIGS. 4A-4B, the gas compressor 109 and the condenser 110 of the vacuum assisted dehydration system 100 are positioned over a saddle member 124 extending outwards from the vacuum chamber 101.

FIG. 4B shows a push fit connection of the sealing member 103 to an opening 104 of the vacuum chamber 101. As exemplarily illustrated in FIG. 4B, in an embodiment, the sealing member 103 is, for example, a push fit seal comprising the metallic cap 121 and the rubber washer 122. The sealing member 103 push fits to the first opening 104 defined at the first opposing end 101a of the vacuum chamber 101 to facilitate an air tight seal of the vacuum chamber 101. The sealing member 103 push fits onto a locking groove 125 positioned proximal to the first opening 104 of the vacuum chamber 101. In an embodiment, the sealing member 103 is turned, for example, in a clockwise direction to lock the sealing member 103 under the locking groove 125, and turned in a counterclockwise direction to unlock the sealing member 103 from under the locking groove 125. In another embodiment, the sealing member 103 is made of a metallic material having a low coefficient of thermal expansion to avoid expansion of the sealing member 103 due to heat produced by the heating coil 107 exemplarily illustrated in FIG. 3A. The metallic material of the sealing member 103 is, for example, aluminum, stainless steel, etc.

Figure 5:
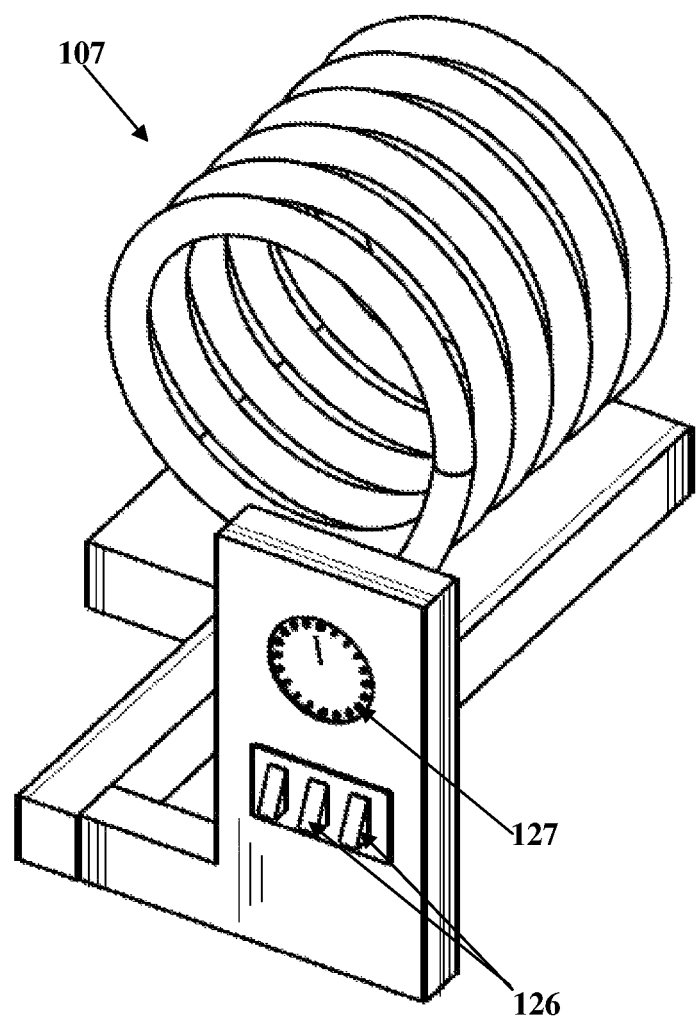
FIG. 5 exemplarily illustrates a rear perspective view of a heating coil of an embodiment of the vacuum assisted dehydration system, showing safety switches operably connected to the heating coil.

FIG. 5 exemplarily illustrates a rear perspective view of the heating coil 107 of an embodiment of the vacuum assisted dehydration system 100 exemplarily illustrated in FIG. 1 and FIG. 3A, showing safety switches 126 operably connected to the heating coil 107. In an embodiment, the heating coil 107 is, for example, an electric heating coil configured to heat the recirculating gas in the vacuum chamber 101 exemplarily illustrated in FIG. 1 and FIG. 3A, to a preset temperature, for example, to a temperature between about 30° C. to about 75° C. to facilitate the evaporation of moisture present in the interstitial cavities 117 and on the surfaces 118 of the accommodated instruments 108 exemplarily illustrated in FIGS. 3A-3B. Since excess temperature may damage an instrument 108, in an embodiment, the vacuum assisted dehydration system 100 further comprises safety switches 126 operably connected to the heating coil 107 to regulate the temperature to a predetermined level in the inner enclosed space 102 of the vacuum chamber 101 exemplarily illustrated in FIG. 3A. A user can manually adjust the temperature settings within the vacuum chamber 101, or the temperature can be adjusted automatically by setting a temperature within a predetermined range of temperatures according to the type and material of the instrument 108 to be dehydrated. The temperatures can be set using a temperature gauge 127 operably connected to the heating coil 107.

Figure 6:
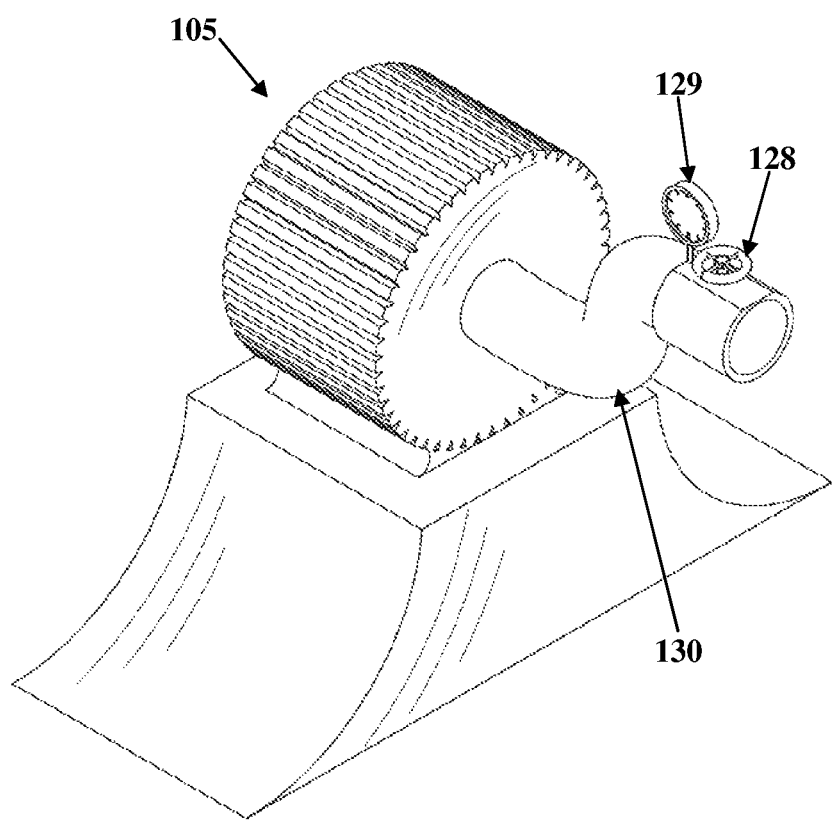
FIG. 6 exemplarily illustrates a top perspective view of the vacuum pump of an embodiment of the vacuum assisted dehydration system, showing a pressure control valve connected to the vacuum pump.

FIG. 6 exemplarily illustrates a top perspective view of the vacuum pump 105 of an embodiment of the vacuum assisted dehydration system 100 exemplarily illustrated in FIG. 1 and FIG. 3A, showing a pressure control valve 128 connected to the vacuum pump 105. In an embodiment, the vacuum pump 105 is, for example, a multistage centrifugal vacuum pump or a multistage reciprocating vacuum pump with a power rating of, for example, about 1 horsepower to about 5 horsepower. In an embodiment, the vacuum assisted dehydration system 100 further comprises a pressure control valve 128 operably connected to the vacuum pump 105 for controlling an amount of the negative gas pressure created within the inner enclosed space 102 of the vacuum chamber 101 to protect the accommodated instruments 108 within the vacuum chamber 101 and to control the rate and extent of moisture evaporation of the moisture off the instruments 108 as exemplarily illustrated in FIG. 3A. A pressure gauge 129 is operably connected to the vacuum pump 105, for example, via a flexible tube 130, for example, a hose, a pipe, etc., to measure and display the negative pressure created within the inner enclosed space 102 of the vacuum chamber 101. A user can set the negative pressure in the vacuum chamber 101 by adjusting the pressure control valve 128. In an embodiment, the vacuum pump 105 draws down the vacuum in the vacuum chamber 101 to a preset negative pressure, for example, a negative pressure of between about 2 inches of mercury and 29 inches of mercury. In an embodiment, the vacuum pump 105 is operably connected to the second opening 106 of the vacuum chamber 101 through a flexible tube 130, for example, a hose, a pipe, etc., as exemplarily illustrated in FIG. 3A.

Figure 7:
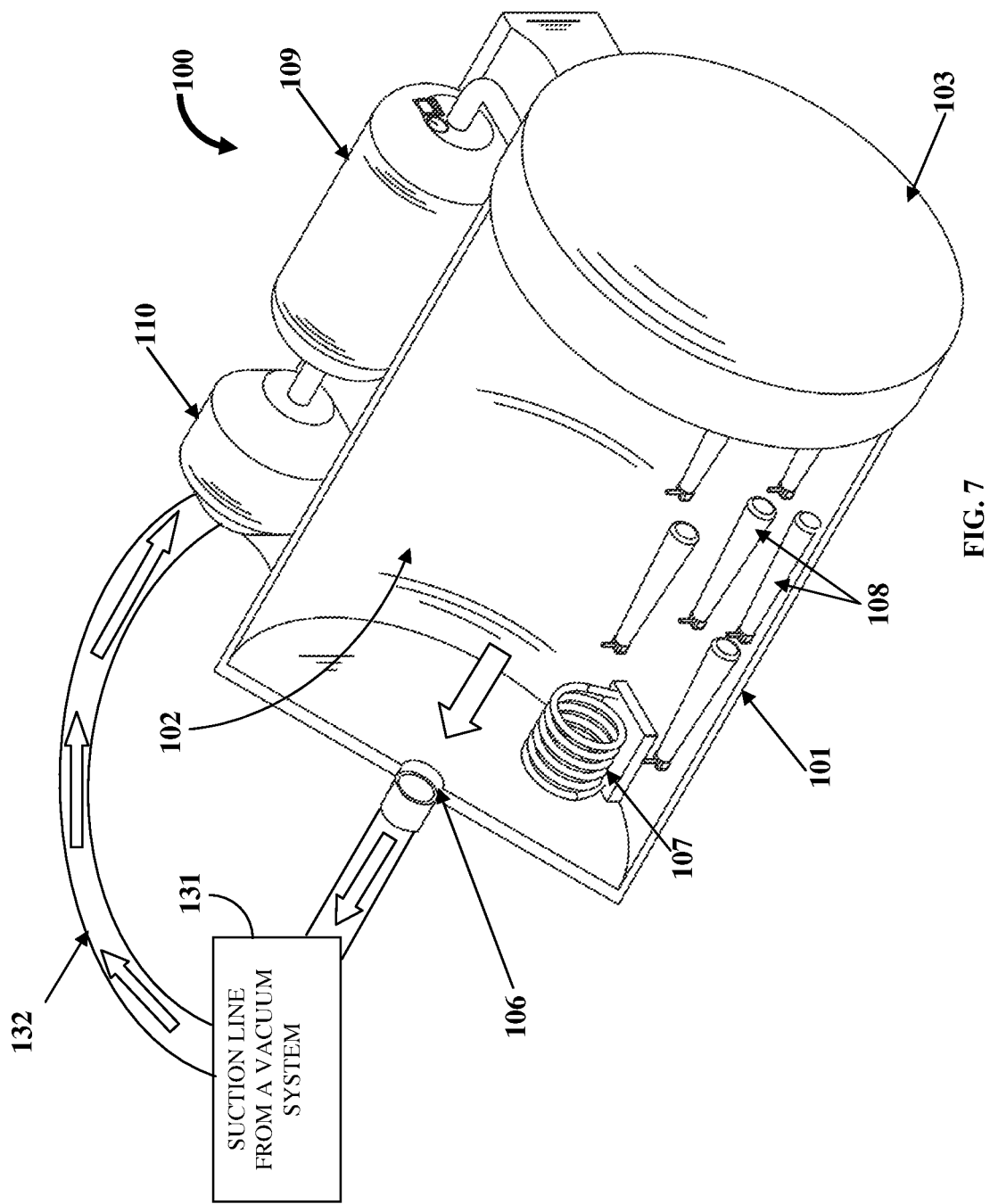
FIG. 7 exemplarily illustrates a cutaway view of an embodiment of the vacuum assisted dehydration system, showing a suction line connected to an opening of the vacuum chamber.

FIG. 7 exemplarily illustrates a cutaway view of an embodiment of the vacuum assisted dehydration system 100, showing a suction line 131 connected to an opening 106 of the vacuum chamber 101. In an embodiment, the vacuum assisted dehydration system 100 disclosed herein further comprises the suction line 131, for example, a dental suction line or a medical plumbing line from a dental or medical vacuum system known in the art, operably connected to the second opening 106 of the vacuum chamber 101. The suction line 131 is a line drawn from one or more dental or medical vacuum systems that can create a negative gas pressure within the vacuum chamber 101 similar to the vacuum pump 105 exemplarily illustrated in FIG. 3A and FIG. 6. An example of a dental vacuum system is a dental suction pump. The suction line 131 produces a preset vacuum pressure, for example, preset to a negative pressure of between about 2 inches of mercury and 29 inches of mercury within the inner enclosed space 102 of the vacuum chamber 101. Similar to the vacuum pump 105 exemplarily illustrated in FIG. 3A and FIG. 6, the suction line 131 is also in fluid communication with the condenser 110 via a suction outlet pipe 132 to transfer the vaporized moisture entrained in the recirculating gas from the inner enclosed space 102 of the vacuum chamber 101 to the condenser 110, to allow the dehydration of the instruments 108 positioned in the inner enclosed space 102 of the vacuum chamber 101 as exemplarily illustrated in FIG. 3A. The vaporized moisture entrained in the recirculating gas is exhausted from the suction line 131 to the condenser 110 via the suction outlet pipe 132.

Figure 8:
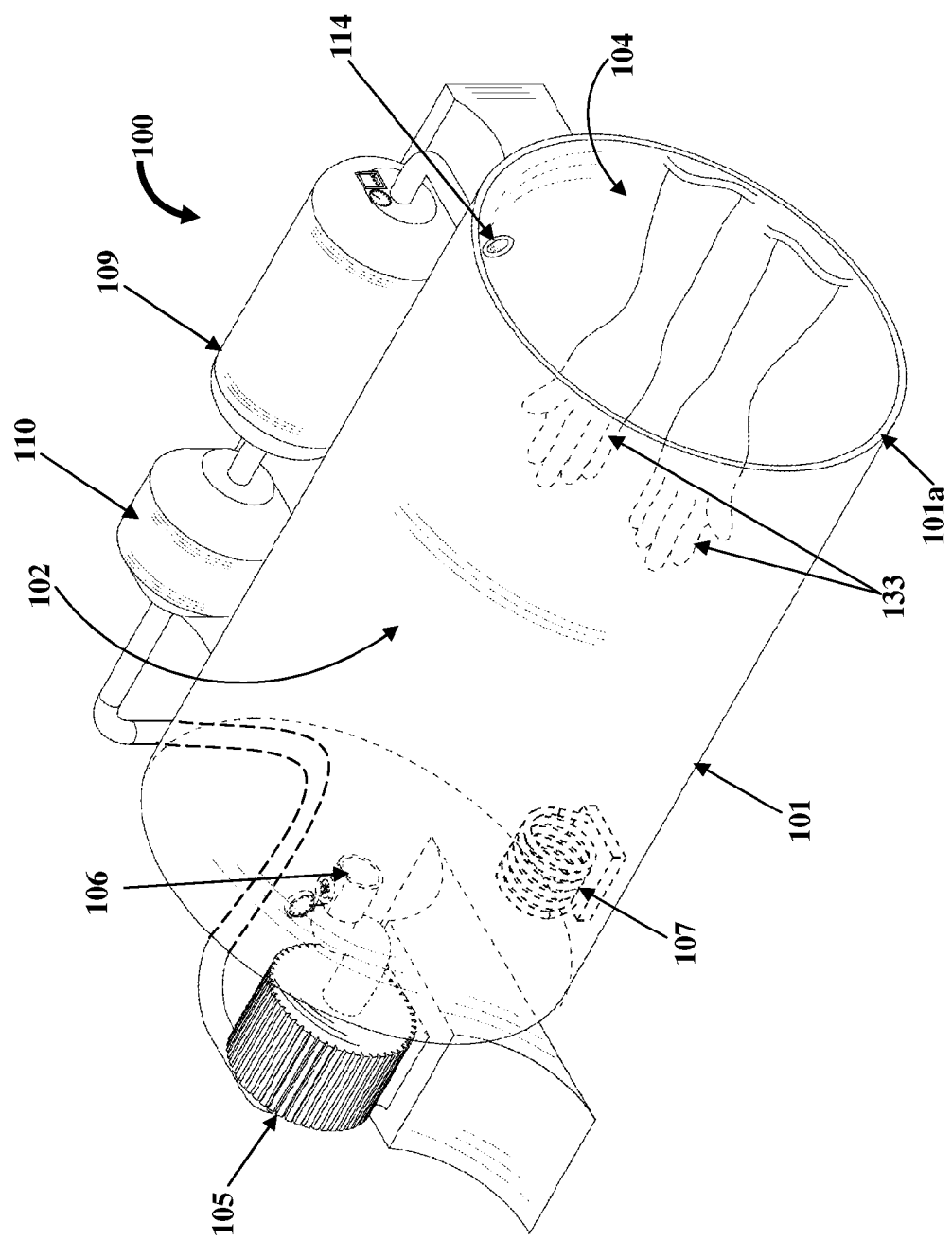
FIG. 8 exemplarily illustrates a top perspective view of an embodiment of the vacuum assisted dehydration system, showing components the surface of which are moist, introduced into an inner enclosed space of the vacuum chamber via an opening.

FIG. 8 exemplarily illustrates a top perspective view of an embodiment of the vacuum assisted dehydration system 100, showing components the surface of which are moist, hereinafter referred to as "moist hands", introduced into an inner enclosed space 102 of the vacuum chamber 101 via an opening 104. In this embodiment, the vacuum assisted dehydration system 100 does not comprise the sealing member 103 exemplarily illustrated in FIGS. 1-4B and FIG. 7. The sealing member 103 is removed to enable a user to introduce moist hands 133 into the inner enclosed space 102 of the vacuum chamber 101 through the first opening 104. The vacuum assisted dehydration system 100 disclosed herein dehydrates a user's moist hands 133, moist surgical gloves, etc., in a dental environment or a medical environment. The vacuum assisted dehydration system 100 comprises the generally cylindrical vacuum chamber 101, the condenser 110, the gas compressor 109, the gas inlet port 114, the heating coil 107, and the vacuum pump 105 as disclosed in the detailed description of FIGS. 1-2 and FIG. 3A. The first opening 104 is defined at the first opposing end 101a of the vacuum chamber 101 and is configured to receive the moist hands 133 into the inner enclosed space 102 of the vacuum chamber 101.

In an example, a user introduces his/her hands 133 the surface of which is moist, into the inner enclosed space 102 of the vacuum chamber 101 through the first opening 104. The recirculating gas heated by the heating coil 107 to a preset temperature of between 30° C. and 75° C. contacts the moist hands 133, transfers heat energy onto the surface of the moist hands 133 to vaporize moisture present on the moist hands 133, and removes moisture present on the moist hands 133. The vacuum pump 105 positioned and operably connected to the second opening 106 of the vacuum chamber 101 creates a negative gas pressure in the inner enclosed space 102 to dehydrate the moist hands 133 and exhausts the vaporized moisture entrained in the heated recirculating gas from the inner enclosed space 102 of the vacuum chamber 101 to the condenser 110.

In this embodiment, the vacuum assisted dehydration system 100 provides a transient dehydration region in the inner enclosed space 102 of the vacuum chamber 101 for dehydrating the moist hands 133 by supplying the recirculating gas from the gas compressor 109 into the inner enclosed space 102 of the vacuum chamber 101, heating the recirculating gas using the heating coil 107, allowing the heated recirculating gas to contact the moist hands 133, and exhausting the vaporized moisture entrained in the heated recirculating gas from the moist hands 133 using the vacuum pump 105 to the condenser 110. In this embodiment, the recirculated air is used to dry moist hands 133 in the open vacuum chamber 101. The vacuum assisted dehydration system 100 produces a transient dehydration state in the vacuum chamber 101, in which moderately heated and moderately pressurized recirculating gas, for example, gas heated to a temperature of about 50° C. and pressurized to between about 16 psig and 25 psig is blown into the inner enclosed space 102 of the vacuum chamber 101. The vaporized moisture entrained in the heated recirculating gas is exhausted by the vacuum pump 105 into the condenser 110. Moist hands 133 which are hard to fit into gloves due to moisture induced friction can be dehydrated rapidly in the open vacuum chamber 101 of the vacuum assisted dehydration system 100.

Figure 9:
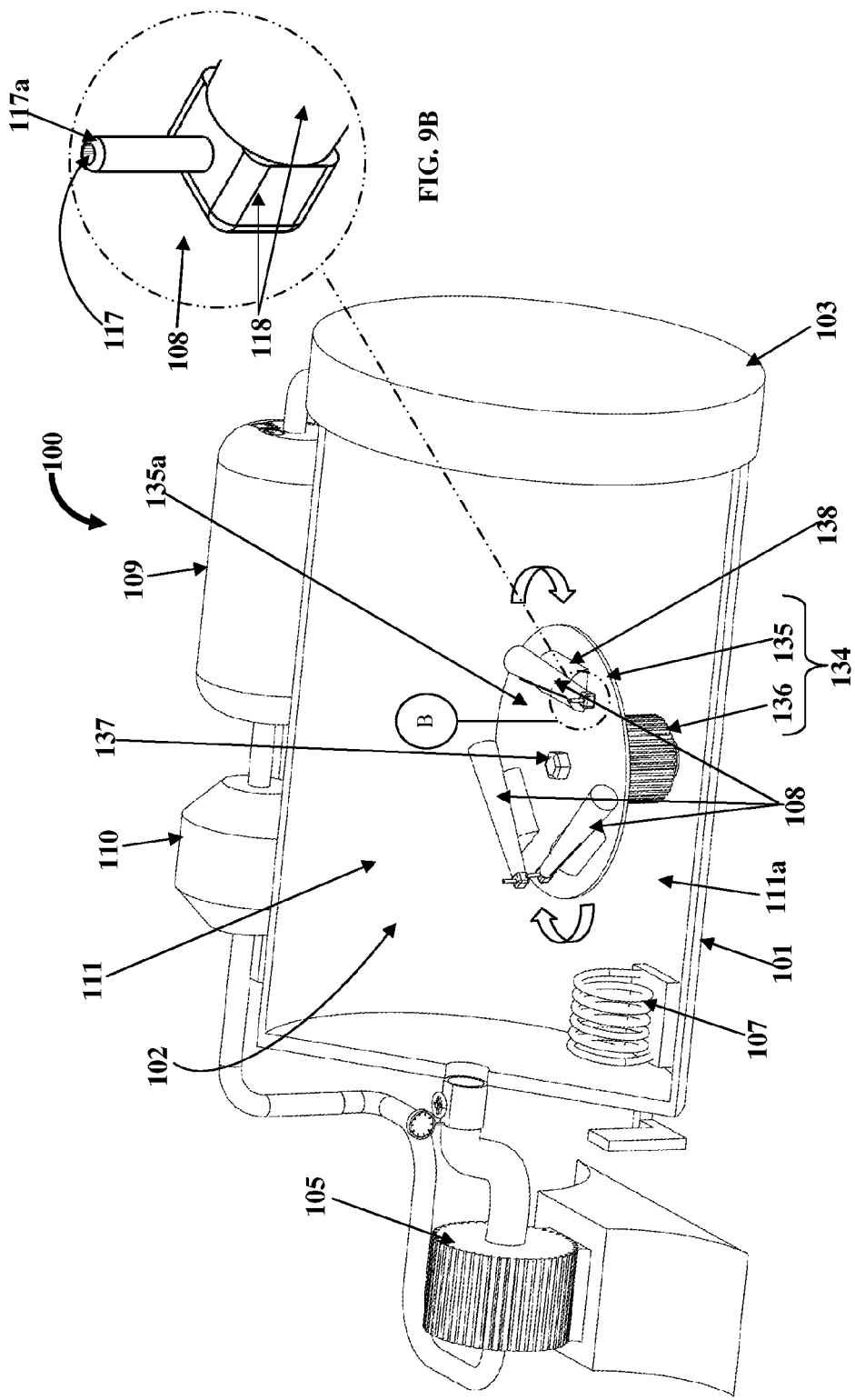
FIG. 9A exemplarily illustrates a cutaway view of an embodiment of the vacuum assisted dehydration system, showing a rotary disk assembly positioned in the vacuum chamber.
FIG. 9B exemplarily illustrates an enlarged view of a portion marked B in FIG. 9A of the embodiment of the vacuum assisted dehydration system, showing interstitial cavities and surfaces of an instrument.

FIG. 9A exemplarily illustrates a cutaway view of an embodiment of the vacuum assisted dehydration system 100, showing a rotary disk assembly 134 positioned in the vacuum chamber 101. In an embodiment, the vacuum assisted dehydration system 100 disclosed herein further comprises the rotary disk assembly 134 positioned on the inner surface wall 111a of the vacuum chamber 101. The rotary disk assembly 134 comprises a disk member 135 and an electric motor 136. The disk member 135 is axially aligned and fixedly connected to the electric motor 136, for example, via a locking nut 137. The disk member 135 fixedly accommodates the instruments 108. The electric motor 136 is, for example, a vertically oriented electric motor. The sealing member 103 is opened and the instruments 108 are introduced into the inner enclosed space 102 of the vacuum chamber 101. The instruments 108 are removably attached on gripping members 138 fixedly attached on an upper surface 135a of the disk member 135, and the instruments 108 are positioned so that when the disk member 135 is rotated at high revolutions per minute (rpm), the moisture within the interstitial cavities 117 of the instruments 108 is forced towards the open ends or open surfaces of the instruments 108. The sealing member 103 is then closed and the electric motor 136 is actuated to rotate the disk member 135 at a speed of, for example, about 400 rpm to about 4000 rpm. The centrifugal force generated on the instruments 108 forces the moisture present in the interstitial cavities 117 and on the surfaces 118 of the instruments 108 towards the open, or upper surfaces 118 of the instruments 108, or the open ends 117a of the interstitial cavities 117 of the instruments 108 as exemplarily illustrated in FIG. 9B. FIG. 9B exemplarily illustrates an enlarged view of a portion marked B in FIG. 9A of the embodiment of the vacuum assisted dehydration system 100, showing interstitial cavities 117 and surfaces 118 of an instrument 108. The moisture in the interstitial cavities 117 of the instruments 108 displaced to the open or outer ends 117a of the interstitial cavities 117 is further removed by the moisture reduced, low humidity recirculating gas supplied by the gas compressor 109 into the inner enclosed space 102 of the vacuum chamber 101, by the recirculating gas that is heated by the heating coil 107, and by the negative gas pressure created in the vacuum chamber 101 by the vacuum pump 105 as disclosed in the detailed description of FIGS. 3A-3B.

Figure 10:
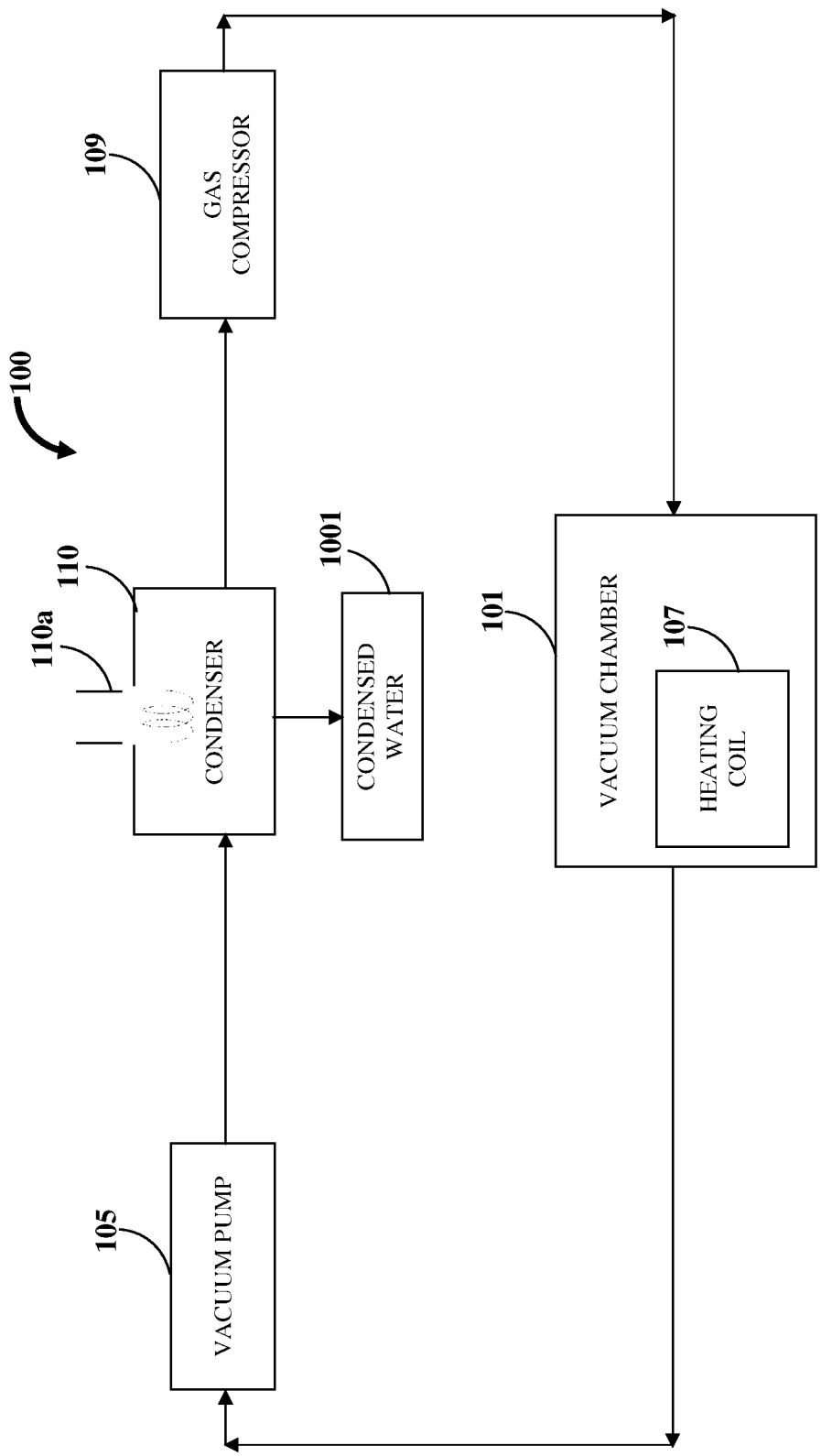
FIG. 10 exemplarily illustrates a block diagram showing a process for dehydrating instruments within the vacuum assisted dehydration system.

FIG. 10 exemplarily illustrates a block diagram showing a process for dehydrating instruments 108 within the vacuum assisted dehydration system 100. The moisture removal process is a recirculating loop shown schematically in FIG. 10. As exemplarily illustrated in FIG. 3A, the instruments 108 from which moisture is to be removed are positioned within the inner enclosed space 102 of the vacuum chamber 101 of the vacuum assisted dehydration system 100. The gas compressor 109 supplies a recirculating gas pressurized to a preset pressure, for example, preset to a pressure between about 16 psig and 45 psig, into the inner enclosed space 102 of the vacuum chamber 101. The recirculating gas is heated by the heating coil 107 to a preset temperature, for example, a temperature preset between about 30° C. to 75° C. The heated recirculating gas contacts the instruments 108 positioned in the inner enclosed space 102 of the vacuum chamber 101; the heated recirculating gas and the vacuum within the vacuum chamber 101 vaporize the moisture from the interstitial cavities 117 and surfaces 118 of the instruments 108 exemplarily illustrated in FIG. 3B.

The vacuum pump 105 creates a preset negative pressure, for example, a negative pressure set between about 2 inches of mercury and 29 inches of mercury in the inner enclosed space 102 of the vacuum chamber 101, which vaporizes the moisture off the instruments 108 and exhausts the vaporized moisture entrained in the heated recirculating gas to the condenser 110 via the vacuum pump outlet pipe 119 exemplarily illustrated in FIG. 3A. The inner enclosed space 102 within the vacuum chamber 101 is maintained at a negative pressure, preset at a negative pressure of between about 2 inches mercury and about 29 inches mercury to allow the moisture in the interstitial cavities 117 and surfaces 118 of the instruments 108 to volatize off the instruments 108 and be entrained in the recirculating gas in the vacuum chamber 101. The recirculating gas from the vacuum chamber 101 is exhausted by the vacuum pump 105 to the condenser 110 where the moisture is condensed out by dropping the temperature of the vaporized moisture entrained in the recirculating gas in the condenser 110. The condenser 110 condenses the vaporized moisture in the recirculating gas to water 1001 by contacting the recirculating gas with a cooling coil 110a in which a refrigerant is recirculated at a preset temperature, for example, a temperature preset between about 10° C. to about −2° C. The moisture reduced, low humidity recirculating gas is fed from the condenser 110 to the gas compressor 109 via the condenser outlet pipe 120 exemplarily illustrated in FIG. 3A. The moisture reduced, low humidity recirculating gas is pumped by the gas compressor 109 at a preset pressure, for example, a pressure between about 15 psig and 40 psig back into the inner closed space 102 of the vacuum chamber 101.

Figure 11A:
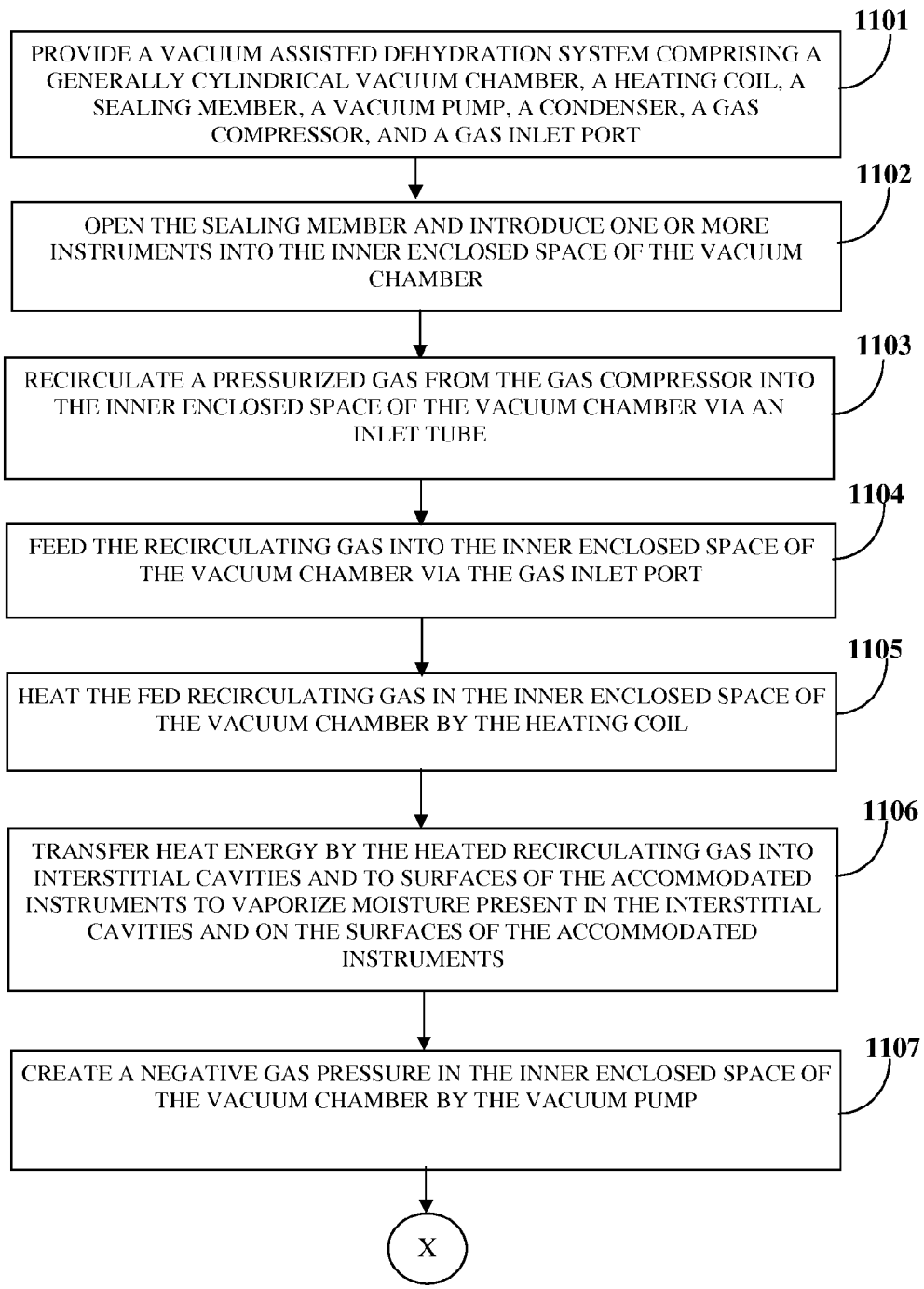
FIGS. 11A-11B exemplarily illustrate a method for dehydrating one or more instruments.
Figure 11B:
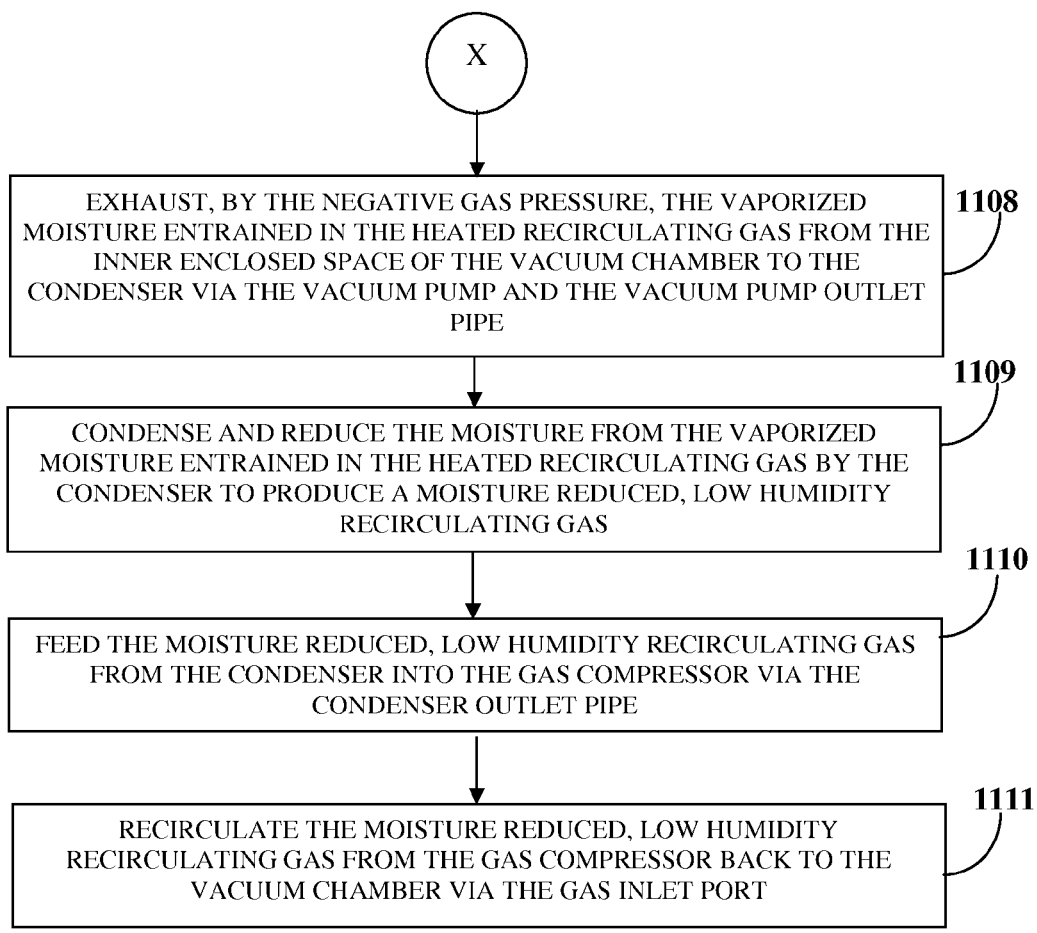

FIGS. 11A-11B exemplarily illustrate a method for dehydrating one or more instruments 108. The vacuum assisted dehydration system 100 comprising the generally cylindrical vacuum chamber 101, the heating coil 107, the sealing member 103, the vacuum pump 105, the condenser 110, the gas compressor 109, and the gas inlet port 114 as exemplarily illustrated in FIGS. 3A-3B and as disclosed in the detailed description of FIGS. 3A-3B is provided 1101. The sealing member 103 is opened to allow a user to introduce 1102 one or more instruments 108 into the inner enclosed space 102 of the vacuum chamber 101. The gas compressor 109 recirculates 1103 a gas pressurized to a preset pressure, for example, a pressure between about 15 psig and 40 psig into the inner enclosed space 102 of the vacuum chamber 101 via the inlet tube 112. The recirculating gas is fed 1104 from the gas compressor 109 into the inner enclosed space 102 of the vacuum chamber 101 via the gas inlet port 114.

The heating coil 107 heats 1105 the fed recirculating gas in the inner enclosed space 102 of the vacuum chamber 101 to a preset temperature, for example, to a temperature between about 30° C. and about 75° C. The heated recirculating gas contacts the instruments 108 positioned within the inner enclosed space 102 of the vacuum chamber 101 and transfers 1106 heat energy into interstitial cavities 117 and to the surfaces 118 of the instruments 108 to vaporize moisture present in the interstitial cavities 117 and on the surfaces 118 of the instruments 108 under a vacuum created in the inner enclosed space 102 by the vacuum pump 105. The vacuum pump 105 creates 1107 a negative gas pressure in the inner enclosed space 102 of the vacuum chamber 101 and exhausts 1108 the vaporized moisture entrained in the heated recirculating gas from the inner enclosed space 102 of the vacuum chamber 101 to the condenser 110 via the vacuum pump 105 and the vacuum pump outlet pipe 119. The condenser 110 condenses 1109 and reduces moisture from the vaporized moisture entrained in the heated recirculating gas to produce a moisture reduced, low humidity recirculating gas. The moisture reduced, low humidity recirculating gas is fed 1110 from the condenser 110 through the condenser outlet pipe 120 into the gas compressor 109. The moisture reduced, low humidity recirculating gas is recirculated 1011 from the gas compressor 109 back to the vacuum chamber 101 via the gas inlet port 114. The embodiment of the vacuum assisted dehydration system 100 exemplarily illustrated in FIG. 8, is used for dehydrating moist components, for example, moist hands 133, moist gloves, etc.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention in its aspects.

We claim:

1. A vacuum assisted dehydration system for dehydrating one or more instruments, said vacuum assisted dehydration system comprising:

a generally cylindrical vacuum chamber comprising a surface wall, said surface wall defining an inner enclosed space configured to accommodate said one or more instruments, said generally cylindrical vacuum chamber further comprising a first opening defined at a first opposing end and a second opening defined at a second opposing end, said generally cylindrical vacuum chamber extending along a horizontal direction from said first opposing end to said second opposing end, said surface wall of said generally cylindrical vacuum chamber configured to reflect heat;

a sealing member removably attached to said first opening, said sealing member configured to open said generally cylindrical vacuum chamber to allow said one or more instruments to be introduced into said inner enclosed space of said generally cylindrical vacuum chamber;

a gas compressor in fluid communication with said generally cylindrical vacuum chamber via an inlet tube, said gas compressor configured for recirculating a gas pressurized to a preset pressure into said inner enclosed space of said generally cylindrical vacuum chamber via said inlet tube;

a gas inlet port defined on said surface wall of said generally cylindrical vacuum chamber and in fluid communication with said gas compressor via said inlet tube, said gas inlet port configured to feed said recirculating gas from said gas compressor into said inner enclosed space of said generally cylindrical vacuum chamber via said inlet tube;

a heating coil operably positioned on said surface wall, said surface wall reflecting heat generated from said heating coil, said heating coil is configured to heat said recirculating gas in said inner enclosed space of said generally cylindrical vacuum chamber, wherein said heated recirculating gas contacts said accommodated one or more instruments positioned in said inner enclosed space of said generally cylindrical vacuum chamber and transfers heat energy into interstitial cavities and to surfaces of said accommodated one or more instruments to vaporize moisture present in said interstitial cavities and on said surfaces of said accommodated one or more instruments, and wherein said heating coil is operably connected to one or more safety switches and at least one temperature gauge, said one or more safety switches configured to regulate temperature within said inner enclosed space to a predetermined level and said at least one temperature gauge configured to control heating of said recirculating gas within said inner enclosed space to a preset temperature;

a vacuum pump operably connected to said second opening, wherein said vacuum pump is in fluid communication with said generally cylindrical vacuum chamber via said second opening, and wherein said vacuum pump is configured to create a negative gas pressure in said inner enclosed space of said generally cylindrical vacuum chamber to dehydrate said accommodated one or more instruments after said generally cylindrical vacuum chamber is closed by said sealing member, and exhaust said vaporized moisture entrained in said heated recirculating gas from said inner enclosed space of said generally cylindrical vacuum chamber; and a rotary disk assembly positioned on an inner said surface wall of said generally cylindrical vacuum chamber, wherein said rotary disk assembly comprises a disk member and an electric motor, wherein said disk member is axially aligned and fixedly connected to said electric motor and configured to fixedly accommodate said one or more instruments, and wherein said electric motor is configured to rotate said disk member at a sufficient speed to generate a centrifugal force sufficient to force said moisture present in said interstitial cavities and on said surfaces of said accommodated one or more instruments to open ends and open surfaces of said accommodated one or more instruments for removal by said recirculating gas fed by said gas compressor into said inner enclosed space of said generally cylindrical vacuum chamber, by said recirculating gas heated by said heating coil, and by said negative gas pressure created in said generally cylindrical vacuum chamber by said vacuum pump.

2. The vacuum assisted dehydration system of claim 1, further comprising a condenser in upstream communication with said vacuum pump via a vacuum pump outlet pipe, and in downstream communication with said gas compressor via a condenser outlet pipe, wherein said condenser is configured to receive said vaporized moisture entrained in said heated recirculating gas from said vacuum pump, and wherein said condenser is further configured to condense and reduce moisture from said vaporized moisture entrained in said heated recirculating gas exhausted from said generally cylindrical vacuum chamber by said vacuum pump, and feed a moisture reduced, low humidity recirculating gas into said gas compressor.

3. The vacuum assisted dehydration system of claim 1, wherein said gas is an inert gas.

4. The vacuum assisted dehydration system of claim 1, wherein said heating coil is an electric heating coil.

5. The vacuum assisted dehydration system of claim 1, wherein said surface wall of said generally cylindrical vacuum chamber is made of aluminum.

6. The vacuum assisted dehydration system of claim 1, wherein said sealing member is a metallic cap concentrically aligned with a washer, wherein said metallic cap is fastened through threads configured at said first opening defined at said first opposing end of said generally cylindrical vacuum chamber.

7. The vacuum assisted dehydration system of claim 1, wherein said sealing member is a push fit seal comprising a metallic cap and a washer, wherein said sealing member is configured to push fit to said first opening defined at said first opposing end of said generally cylindrical vacuum chamber to facilitate an air tight seal of said generally cylindrical vacuum chamber.

8. The vacuum assisted dehydration system of claim 1, wherein said vacuum pump is one of a multistage centrifugal vacuum pump and a multistage reciprocating vacuum pump.

9. The vacuum assisted dehydration system of claim 1, wherein said vacuum pump is operably connected to said second opening of said generally cylindrical vacuum chamber through one of a hose and a pipe.

10. The vacuum assisted dehydration system of claim 1, further comprising one or more pressure control valves operably connected to said vacuum pump, wherein said one or more pressure control valves are configured to control an amount of said negative gas pressure created within said inner enclosed space of said generally cylindrical vacuum chamber to protect said accommodated one or more instruments within said generally cylindrical vacuum chamber.

* * * * *